(12) United States Patent
Kano et al.

(10) Patent No.: US 11,037,680 B2
(45) Date of Patent: Jun. 15, 2021

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Yusuke Kano, Nasushiobara (JP); Kazumasa Noro, Shioya (JP); Longxun Piao, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 399 days.

(21) Appl. No.: 15/955,893

(22) Filed: Apr. 18, 2018

(65) Prior Publication Data
US 2018/0330821 A1    Nov. 15, 2018

(30) Foreign Application Priority Data
Apr. 18, 2017 (JP) ............................. JP2017-082084

(51) Int. Cl.
G16H 50/20 (2018.01)
G16H 50/70 (2018.01)
(Continued)

(52) U.S. Cl.
CPC ............. *G16H 50/20* (2018.01); *A61B 5/743* (2013.01); *G16H 10/60* (2018.01); *G16H 40/20* (2018.01);
(Continued)

(58) Field of Classification Search
CPC ........ G16H 50/20; G16H 40/20; G16H 10/60; G16H 50/70; G16H 70/20; G16H 80/00;
(Continued)

(56) References Cited

U.S. PATENT DOCUMENTS

| | | | | |
|---|---|---|---|---|
| 2010/0177950 A1* | 7/2010 | Donovan | ............... | G16H 50/30 382/133 |
| 2012/0221350 A1* | 8/2012 | Kenedy | ................. | G06F 16/951 705/2 |
| 2013/0304499 A1* | 11/2013 | Rangadass | ..... | G06Q 10/063114 705/2 |

FOREIGN PATENT DOCUMENTS

JP   2009-093309   4/2009

OTHER PUBLICATIONS

T. Tanioka et al., "Outcome management and morphologic variance analysis using psychomsTM for patient care in psychiatric hospitals," 2007 International Conference on Natural Language Processing and Knowledge Engineering, Beijing, 2007, pp. 502-506 , doi: 10.1109/NLPKE.2007.4368078. (Year: 2007).*

* cited by examiner

*Primary Examiner* — Elaine Gort
*Assistant Examiner* — Amanda R. Covington
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry obtains data on medical actions and data on differences between planned medical actions or achievement objectives of treatment and results thereof. The processing circuitry extracts relevant factors associated with the differences based on the data on the medical actions and the data on the differences. The processing circuitry the relevant factors by allocating elements included in classification criteria to the relevant factors. The processing circuitry displays the relevant factors on a display for each of the classification criteria.

16 Claims, 15 Drawing Sheets

(51) Int. Cl.
*G16H 10/60* (2018.01)
*G16H 40/20* (2018.01)
*G16H 70/20* (2018.01)
*G16H 15/00* (2018.01)
*G16H 10/20* (2018.01)
*A61B 5/00* (2006.01)
*G16H 80/00* (2018.01)
*A61B 6/00* (2006.01)

(52) U.S. Cl.
CPC ............. *G16H 50/70* (2018.01); *G16H 70/20* (2018.01); *G16H 80/00* (2018.01); *A61B 6/5217* (2013.01); *A61B 6/563* (2013.01); *G16H 10/20* (2018.01); *G16H 15/00* (2018.01)

(58) Field of Classification Search
CPC ........ G16H 15/00; G16H 10/20; A61B 5/743; A61B 6/5217; A61B 6/563; G06F 19/30; G06F 19/32; G06F 19/34; G06Q 50/22; G06Q 50/24
See application file for complete search history.

FIG.2

| PATHWAY NAME | PATHWAY CODE | MEDICAL ACTION/ OUTCOME | SCHEDULED DATE OF IMPLEMENTATION |
|---|---|---|---|
| COLECTOMY | P0001 | VITAL CHECK | 1 |
| COLECTOMY | P0001 | REGULAR DIET | 1 |
| COLECTOMY | P0001 | PURSENNID | 2 |
| ESOPHAGECTOMY | P0002 | NO SYMPTOMS OR FINDINGS OF ANASTOMOTIC LEAKAGE | 1 |
| ... | ... | ... | ... |

FIG.3

| PATIENT CODE | PATHWAY CODE | SEX | AGE | DISEASE NAME |
|---|---|---|---|---|
| p01 | P0001 | MALE | 55 | RECTOSIGMOID COLON CANCER |
| p02 | P0022 | FEMALE | 40 | ACUTE CHOLANGITIS |
| p03 | P0008 | MALE | 65 | PANCREATIC HEAD CANCER |
| p04 | P0017 | MALE | 63 | ILEUS |
| ... | ... | ... | ... | ... |

FIG.4

| PATIENT CODE | MEDICAL ACTION/ OUTCOME | ITEM | RESULT | DATE OF IMPLE- MENTATION |
|---|---|---|---|---|
| p01 | VITAL CHECK | IMPLEMENTATION RESULT | IMPLEMENTED | 1 |
| | | SYSTOLIC BLOOD PRESSURE | 160 mmHg | 1 |
| | | SpO2 | 99% | 1 |
| p01 | REGULAR DIET | IMPLEMENTATION RESULT | IMPLEMENTED | 1 |
| | | FOOD INTAKE | 50% | 1 |
| p01 | PURSENNID | IMPLEMENTATION RESULT | UNIMPLEMENTED | 2 |
| p02 | NO SYMPTOMS OR FINDINGS OF ANASTOMOTIC LEAKAGE | ASSESSMENT | ACHIEVED | 1 |
| ... | ... | ... | ... | ... |

FIG.5

| PATIENT CODE | MEDICAL ACTION/ OUTCOME | VARIANCE CODE | DETAILED VARIANCE | DATE OF OCCURRENCE |
|---|---|---|---|---|
| p01 | VITAL SIGN IS STABLE | V0001 | SYSTOLIC BLOOD PRESSURE IS OUT OF PROPER VALUE | 1 |
| p02 | REGULAR DIET | V0004 | INGEST FOOD PRESENTED BY FAMILY | 1 |
| p03 | PURSENNID | V0007 | CHANGE DUE TO ORDER FROM DOCTOR | 2 |
| p04 | NO SYMPTOMS OR FINDINGS OF ANASTOMOTIC LEAKAGE | V0001 | SEEM TO HAVE ABNORMAL ABDOMINAL PAIN | 4 |
| ... | ... | ... | ... | ... |

FIG.6

| VARIANCE CODE | LARGE CATEGORY | VARIANCE CATEGORY |
|---|---|---|
| V0001 | PATIENT FACTOR | PHYSICAL FACTOR |
| V0004 | PATIENT FACTOR | PATIENT'S INTENTION OR WILL |
| V0007 | STAFF FACTOR | ORDER FROM DOCTOR |
| ... | ... | ... |

FIG.7

| ANTECEDENT | CONSEQUENT | SUPPORT | CONFIDENCE | LIFT |
|---|---|---|---|---|
| ABNORMAL ABDOMINAL PAIN (3) | ANASTOMOTIC LEAKAGE (5) | 0.30 | 0.54 | 5.40 |
| ABNORMAL PCT VALUE (4) | ANASTOMOTIC LEAKAGE (5) | 0.23 | 0.73 | 7.30 |
| ABNORMAL ABDOMINAL PAIN (3) +ABNORMAL PCT VALUE (4) | ANASTOMOTIC LEAKAGE (5) | 0.10 | 0.90 | 9.00 |
| REGULAR DIET (2) | ANASTOMOTIC LEAKAGE (4) | 0.94 | 0.30 | 6.00 |
| ... | ... | ... | ... | ... |

FIG.8

| A. PURPOSE CLASSIFICATION | |
|---|---|
| A-1 | PRE-DETECTION |
| A-2 | PREVENTIVE MEASURE |
| A-3 | REVIEW ON EXCLUSION CRITERIA |

| B. MEDICAL CARE COST | |
|---|---|
| B-1 | LOW |
| B-2 | INTERMEDIATE |
| B-3 | HIGH |

| C. ORDER TYPE LARGE CATEGORY | |
|---|---|
| C-1 | EXAMINATION |
| C-2 | MEDICATION |
| C-3 | TREATMENT |
| C-4 | NUTRITION |
| C-5 | OBSERVATION |
| C-6 | ADVICE |
| ... | ... |

| D. ORDER TYPE SMALL CATEGORY | |
|---|---|
| D-1 | SAMPLING |
| D-2 | PHYSIOLOGICAL EXAMINATION |
| D-3 | IMAGE EXAMINATION |
| ... | ... |
| D-10 | PRESCRIPTION |
| D-11 | INJECTION |
| ... | ... |

| E. PHASE | |
|---|---|
| E-1 | PRIOR TO SURGERY |
| E-2 | DAY OF SURGERY |
| E-3 | POSTOPERATIVE DAYS 1 TO 3 |
| E-4 | POSTOPERATIVE DAYS 4 TO 6 |

| F. PHASE (DATE) | |
|---|---|
| F-1 | PREOPERATIVE DAY 2 |
| F-2 | PREOPERATIVE DAY 1 |
| F-3 | DAY OF SURGERY |
| F-4 | POSTOPERATIVE DAY 1 |
| ... | ... |

| I. NUMBER OF TYPES OF LARGE CATEGORY | |
|---|---|
| I-1 | 1 |
| I-2 | 2 |
| I-3 | 3 OR MORE |

| J. NUMBER OF TYPES OF SMALL CATEGORY | |
|---|---|
| J-1 | 1 |
| J-2 | 2 |
| J-3 | 3 OR MORE |

| G. PATIENT ATTRIBUTE | |
|---|---|
| G-1 | AGE |
| G-2 | SEX |
| G-3 | DISEASE NAME |
| ... | ... |

| H. NUMBER OF ANTECEDENTS | |
|---|---|
| H-1 | 1 |
| H-2 | 2-3 |
| H-3 | 4 OR MORE |

| K. RELATION WITH PATHWAY ITEM | |
|---|---|
| K-1 | INCLUDING ONLY ELEMENTS OTHER THAN PATHWAY ITEM |
| K-2 | INCLUDING ELEMENTS OTHER THAN PATHWAY ITEM |
| K-3 | INCLUDING ONLY PATHWAY ITEM |

FIG.9

| ITEM LABEL | A | B | C | D | E | F |
|---|---|---|---|---|---|---|
| ABNORMAL PCT VALUE | A-1 | B-2 | C-1 | D-1 | E-4 | F-7 |
| ABNORMAL ABDOMINAL PAIN | A-1 | B-1 | C-5 | D-22 | E-4 | F-7 |
| ABNORMALITY IN CT EXAMINATION | A-1 | B-3 | C-1 | D-3 | E-3 | F-6 |
| UNDER AGE OF 65 | A-1 A-3 | - | - | - | - | - |
| PREOPERATIVE FASTING | A-2 | B-1 | C-4 | D-18 | E-1 | F-2 |
| PURSENNID | A-2 | B-1 | C-2 | D-10 | E-3 | F-5 |

FIG.10

| SELECTED CLASSIFICATION/ ELEMENT | SELECTABLE CLASSIFICATION/ ELEMENT | UNSELECTABLE CLASSIFICATION/ELEMENT |
|---|---|---|
| A-3. REVIEW ON EXCLUSION CRITERIA | G. PATIENT ATTRIBUTE | A. PURPOSE CLASSIFICATION C. ORDER TYPE LARGE CATEGORY E. PHASE |
| C. ORDER TYPE LARGE CATEGORY | D. ORDER TYPE SMALL CATEGORY I. NUMBER OF TYPES OF LARGE CATEGORY | A. PURPOSE CLASSIFICATION C. ORDER TYPE LARGE CATEGORY G. PATIENT ATTRIBUTE |
| E. PHASE | F. PHASE (DATE) | E. PHASE |
| D. ORDER TYPE SMALL CATEGORY | J. NUMBER OF TYPES OF SMALL CATEGORY | D. ORDER TYPE SMALL CATEGORY |
| ... | ... | ... |

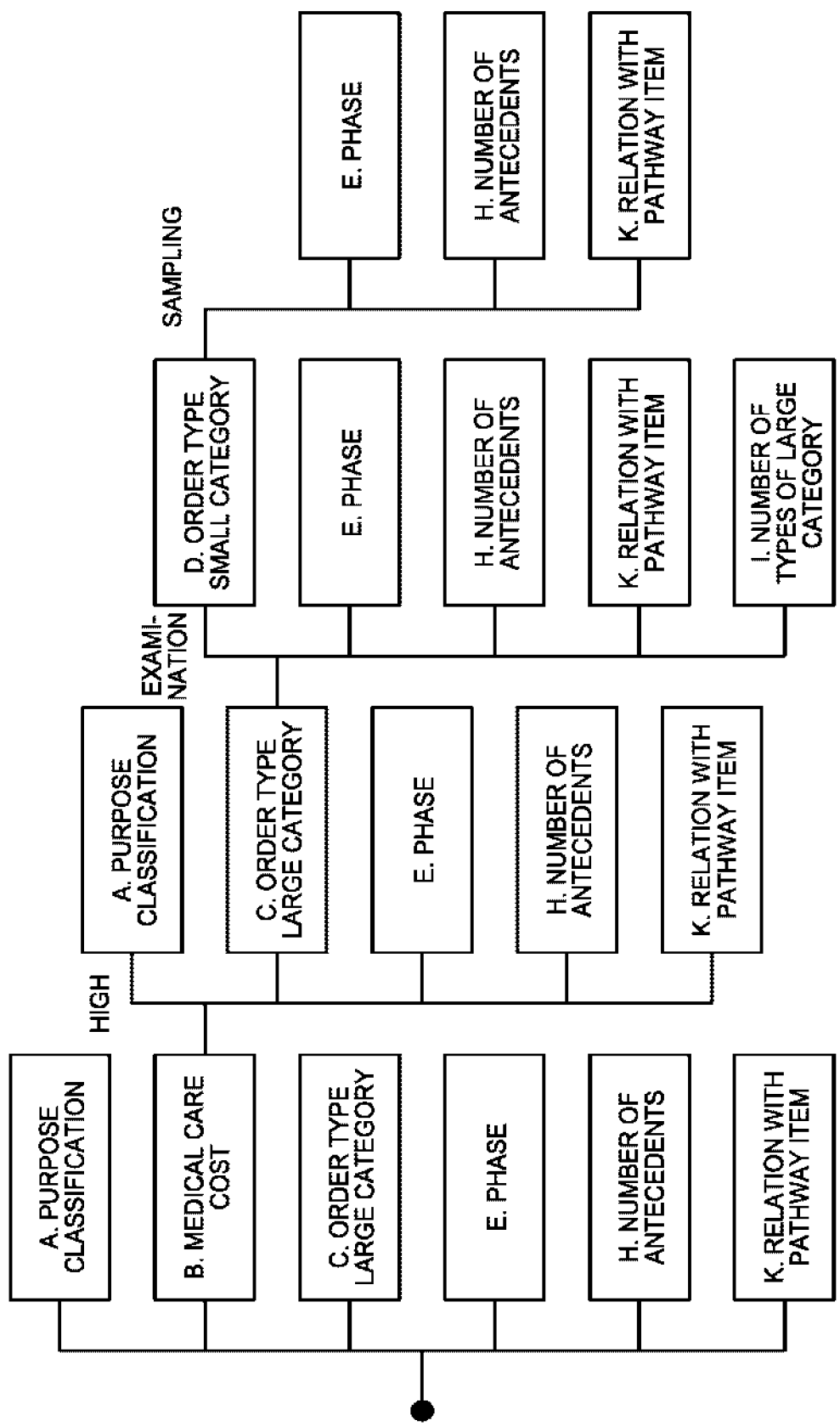

FIG.12

| ANTECEDENT | CONSEQUENT | SUPPORT | CONFIDENCE | LIFT | A | B | ... | K |
|---|---|---|---|---|---|---|---|---|
| ABNORMAL PCT VALUE | ANASTOMOTIC LEAKAGE | 0.30 | 0.54 | 5.40 | A-1 | B-2 | ... | K-3 |
| ABNORMAL PCT VALUE+ABNORMAL ABDOMINAL PAIN | ANASTOMOTIC LEAKAGE | 0.23 | 0.73 | 7.30 | A-1 | B-2 | ... | K-3 |
| ABNORMAL PCT VALUE+ABNORMAL ABDOMINAL PAIN +ABNORMALITY IN CT EXAMINATION | ANASTOMOTIC LEAKAGE | 0.10 | 0.90 | 9.00 | A-1 | - | ... | K-3 |
| ABNORMALITY IN CT EXAMINATION | ANASTOMOTIC LEAKAGE | 0.94 | 0.30 | 3.00 | A-1 | B-3 | ... | K-2 |
| UNDER AGE OF 65 +ABDOMINAL SURGERY | ANASTOMOTIC LEAKAGE | 0.30 | 0.54 | 5.40 | A-1 A-3 | - | ... | K-3 |
| PREOPERATIVE FASTING | ANASTOMOTIC LEAKAGE | 0.23 | 0.73 | 7.30 | A-2 | B-1 | ... | K-2 |
| PURSENNID | ANASTOMOTIC LEAKAGE | 0.10 | 0.90 | 9.00 | A-2 | B-1 | ... | K-3 |
| ... | ... | ... | ... | ... | ... | ... | ... | ... |

FIG.13

| ANTECEDENT | CONSEQUENT | SUPPORT | CONFIDENCE | LIFT | A | B | ... | K |
|---|---|---|---|---|---|---|---|---|
| ABNORMAL PCT VALUE | ANASTOMOTIC LEAKAGE | 0.30 | 0.54 | 5.40 | A-1 | B-2 | ... | K-3 |
| ABNORMAL PCT VALUE +ABNORMAL ABDOMINAL PAIN | ANASTOMOTIC LEAKAGE | 0.23 | 0.73 | 7.30 | A-1 | B-2 | ... | K-3 |
| ABNORMAL PCT VALUE +ABNORMAL ABDOMINAL PAIN +ABNORMALITY IN CT EXAMINATION | ANASTOMOTIC LEAKAGE | 0.10 | 0.90 | 9.00 | A-1 | - | ... | K-3 |
| ABNORMALITY IN CT EXAMINATION | ANASTOMOTIC LEAKAGE | 0.94 | 0.30 | 3.00 | A-1 | B-3 | ... | K-2 |
| UNDER AGE OF 65+ABDOMINAL SURGERY | ANASTOMOTIC LEAKAGE | 0.30 | 0.54 | 5.40 | A-1 A-3 | - | ... | K-3 |
| ... | ... | ... | ... | ... | ... | ... | ... | ... |

| ANTECEDENT | CONSEQUENT | SUPPORT | CONFIDENCE | LIFT | A | B | ... | K |
|---|---|---|---|---|---|---|---|---|
| PREOPERATIVE FASTING | ANASTOMOTIC LEAKAGE | 0.23 | 0.73 | 7.30 | A-2 | B-1 | ... | K-2 |
| PURSENNID | ANASTOMOTIC LEAKAGE | 0.10 | 0.90 | 9.00 | A-2 | B-1 | ... | K-3 |
| ... | ... | ... | ... | ... | ... | ... | ... | ... |

| ANTECEDENT | CONSEQUENT | SUPPORT | CONFIDENCE | LIFT | A | B | ... | K |
|---|---|---|---|---|---|---|---|---|
| UNDER AGE OF 65+ABDOMINAL SURGERY | ANASTOMOTIC LEAKAGE | 0.30 | 0.54 | 5.40 | A-1 A-3 | - | ... | K-3 |
| ... | ... | ... | ... | ... | ... | ... | ... | ... |

FIG.14

| CLASSIFICATION CRITERIA | | CONFIDENCE DISTRIBUTION | RELEVANT FACTORS (HAVING HIGHEST CONFIDENCE) |
|---|---|---|---|
| PURPOSE CLASSIFICATION | PRE-DETECTION | ⋀ 90% | ABNORMAL PCT VALUE — ABNORMAL ABDOMINAL PAIN → ANASTOMOTIC LEAKAGE |
| | PREVENTIVE MEASURE | ⋀ 75% | PREOPERATIVE FASTING → ANASTOMOTIC LEAKAGE |
| | REVIEW ON EXCLUSION CRITERIA | ⋀ 43% | UNDER AGE OF 65 — ABDOMINAL SURGERY → ANASTOMOTIC LEAKAGE |

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2017-082084, filed on Apr. 18, 2017; the entire contents of which are incorporated herein by reference.

FIELD

Embodiments described herein relate generally to a medical information processing apparatus and a medical information processing method.

BACKGROUND

Conventionally, in the medical field, importance has been given to the use of clinical pathways to standardize medical care plans and achieve the improvement of quality in healthcare. To achieve the improvement of quality in healthcare by using clinical pathways, it is important to analyze variance, which is the difference between a clinical pathway and an actual medical care, and continuously deal with the causes of the variance affecting the quality in healthcare. In view of this, a technology for extracting the causes of variance from medical care data accumulated in hospitals or other such facilities and refine and present the extracted causes of the variance has been proposed.

BRIEF DESCRIPTION OF THE DRAWINGS

FIG. 2 is a diagram illustrating an example of clinical pathway data obtained by an obtaining function according to the first embodiment;

FIG. 3 is a diagram illustrating an example of patient data obtained by the obtaining function according to the first embodiment;

FIG. 4 is a diagram illustrating an example of historic data obtained by the obtaining function according to the first embodiment;

FIG. 5 is a diagram illustrating an example of variance data obtained by the obtaining function according to the first embodiment;

FIG. 6 is a diagram illustrating an example of variance code master data obtained by the obtaining function according to the first embodiment;

FIG. 7 is a diagram illustrating an example of association rule data generated by an extracting function according to the first embodiment;

FIG. 8 is a diagram illustrating an example of classification criterion master data used by a classifying function according to the first embodiment;

FIG. 9 is a diagram illustrating an example of classification master data used by the classifying function according to the first embodiment;

FIG. 10 is a diagram illustrating an example of transition rule master data used by the classifying function according to the first embodiment;

FIG. 11 is a diagram illustrating an example of transition of classification criteria defined by the transition rule master data according to the first embodiment;

FIG. 12 is a diagram illustrating an example of allocation of elements of classification criteria performed by the classifying function according to the first embodiment;

FIG. 13 is a diagram illustrating an example of classification of association rule data performed by the classifying function according to the first embodiment;

FIG. 14 is a diagram illustrating an example of extraction results of characteristics of an association rule extracted by an aggregating function according to the first embodiment;

DETAILED DESCRIPTION

A medical information processing apparatus according to an embodiment includes an obtaining unit, an extracting unit, a classifying unit, and a display controlling unit. The obtaining unit obtains data on medical actions and data on differences between planned medical actions or achievement objectives of treatment and results thereof. The extracting unit extracts relevant factors associated with the differences based on the data on the medical actions and the data on the differences. The classifying unit classifies the relevant factors by allocating elements included in classification criteria to the relevant factors. The display controlling unit displays the relevant factors on a display for each classification criterion.

Referring to the accompanying drawings, a medical information processing apparatus and a medical information processing method according to embodiments are described in detail below.

First Embodiment

Figure 1:
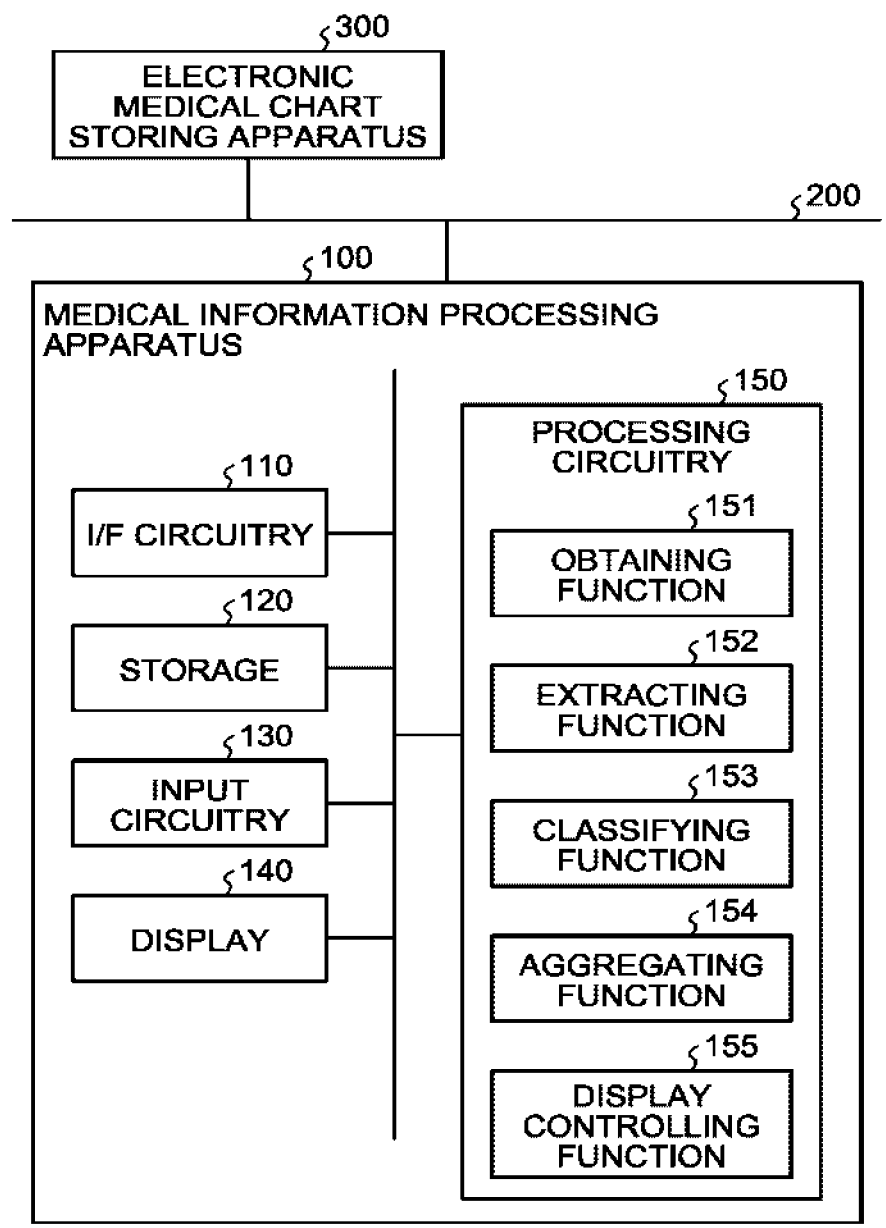
FIG. 1 is a diagram illustrating a configuration example of a medical information processing apparatus according to a first embodiment.

FIG. 1 is a diagram illustrating a configuration example of a medical information processing apparatus according to a first embodiment.

For example, as illustrated in FIG. 1, a medical information processing apparatus 100 according to the first embodiment is communicably connected to an electronic medical chart storing apparatus 300 through a network 200. For example, the medical information processing apparatus 100 and the electronic medical chart storing apparatus 300 are installed in a hospital, and are mutually connected by the network 200, such as an in-hospital local area network (LAN).

The electronic medical chart storing apparatus 300 stores therein medical care data on various kinds of medical care implemented in a hospital. For example, the electronic medical chart storing apparatus 300 is installed as a part of an electronic health record system introduced in the hospital, and stores therein medical care data generated by the electronic health record system. For example, the electronic medical chart storing apparatus 300 is implemented by a computer device such as a database (DB) server, and stores medical care data in a storage, such as a semiconductor memory element such as a random access memory (RAM) and a flash memory, a hard disk, and an optical disc.

The medical information processing apparatus 100 obtains medical care data from the electronic medical chart storing apparatus 300 through the network 200, and uses the obtained medical care data to perform various kinds of information processing. For example, the medical information processing apparatus 100 is implemented by a computer device, such as a workstation.

Specifically, the medical information processing apparatus 100 includes interface (I/F) circuitry 110, a storage 120, input circuitry 130, a display 140, and processing circuitry 150.

The I/F circuitry 110 is connected to the processing circuitry 150, and controls transmission and communication of various kinds of data between the I/F circuitry 110 and the electronic medical chart storing apparatus 300. For example, the I/F circuitry 110 receives medical care data from the electronic medical chart storing apparatus 300, and outputs the received medical care data to the processing circuitry 150. For example, the I/F circuitry 110 is implemented by a network card, a network adapter, or a network interface controller (NIC).

The storage 120 is connected to the processing circuitry 150, and stores various kinds of data therein. For example, the storage 120 stores therein medical care data received from the electronic medical chart storing apparatus 300. For example, the storage 120 is implemented by a semiconductor memory element, such as a random access memory (RAM) and a flash memory, a hard disk, or an optical disc.

The input circuitry 130 is connected to the processing circuitry 150, and converts an input operation received from an operator into an electric signal and outputs the electric signal to the processing circuitry 150. For example, the input circuitry 130 is implemented by a trackball, a switch button, a mouse, a keyboard, or a touch panel.

The display 140 is connected to the processing circuitry 150, and displays various kinds of information and various kinds of image data output from the processing circuitry 150. For example, the display 140 is implemented by a liquid crystal monitor, a cathode ray tube (CRT) monitor, or a touch panel.

The processing circuitry 150 controls the components in the medical information processing apparatus 100 in response to an input operation received from the operator through the input circuitry 130. For example, the processing circuitry 150 stores medical care data output from the I/F circuitry 110 in the storage 120. For example, the processing circuitry 150 reads medical care data from the storage 120, and displays the read medical care data on the display 140. For example, the processing circuitry 150 is implemented by a processor.

The overall configuration of the medical information processing apparatus 100 according to the first embodiment has been described above. With such a configuration, the medical information processing apparatus 100 according to the first embodiment has a function for extracting the causes of variance, which is the difference between a clinical pathway and an actual medical care, from medical care data accumulated in a hospital or other such facilities and effectively refining and presenting the extracted causes of the variance.

Here, the clinical pathway data is a standard medical care plan or medical care flow defined for each treatment purpose and/or disease. That is, the clinical pathway is defined as a standard, and it does not limited to a medical care plan or a medical care flow prepared for each patients.

Further, the variance is a difference between a planned medical action or achievement objective of treatment and a result thereof. More specifically, the variance is a difference between a planned medical action and an actually implemented medical action, or a difference between a planned achievement objective of treatment and an achievement state thereof.

Specifically, the processing circuitry 150 has an obtaining function 151, an extracting function 152, a classifying function 153, an aggregating function 154, and a display controlling function 155. The obtaining function 151 is an example of an obtaining unit. The extracting function 152 is an example of an extracting unit. The classifying function 153 is an example of a classifying unit. The aggregating function 154 is an example of an aggregating unit. The display controlling function 155 is an example of a display controlling unit.

The obtaining function 151 obtains data on medical actions and data on variance that has occurred in the clinical pathway.

Here, For example, the obtaining function 151 obtains, as the data on medical actions, data on medical actions implemented in accordance with a clinical pathway. Moreover, for example, the obtaining function 151 may further obtain, in addition to data on medical actions implemented in accordance with a clinical pathway, data on medical actions not implemented in accordance with a clinical pathway.

Specifically, the obtaining function 151 obtains clinical pathway data, patient data, historic data, variance data, and variance code master data from the electronic medical chart storing apparatus 300. The obtaining function 151 stores the obtained data in the storage 120.

The clinical pathway data is data in which medical actions to be implemented, outcomes to be assessed, and scheduled dates of implementation of the medical actions are recorded for each clinical pathway. The patient data is data in which basic information on patients is recorded. The historic data is data in which the histories of medical actions implemented on patients and care processes for patient conditions are recorded. The variance data is data generated when the care process deviates from the clinical pathway, and is data in which the occurrence date of variance and classification codes and texts representing reasons for the occurrence are recorded. The variance code master data is data in which the classification of variance is recorded.

For example, the obtaining function 151 converts each data obtained from the electronic medical chart storing apparatus 300 into an optimal format for analyzing the clinical pathway, and stores the converted data in the storage 120. In this case, information included in each data is obtained directly from data stored in the electronic medical chart storing apparatus 300, but the embodiments are not limited thereto. For example, when information included in each data includes information that cannot be directly obtained from data stored in the electronic medical chart storing apparatus 300, the obtaining function 151 may convert the information by using a conversion table and store the converted information in the storage 120. In this case, the conversion table is stored in the storage 120 in advance.

For obtaining each data, the obtaining function 151 may obtain only data on patients to which clinical pathways are applied, or may obtain both of data on patients to which clinical pathways are applied and data on patients to which clinical pathways are not applied.

FIG. 2 is a diagram illustrating an example of clinical pathway data obtained by the obtaining function 151 according to the first embodiment.

For example, as illustrated in FIG. 2, the clinical pathway data includes a pathway name, a pathway code, a medical action/outcome, and a scheduled date of implementation as data items. In the pathway name, the name of a clinical pathway is set. In the pathway code, a code for uniquely identifying the clinical pathway is set. In the medical action/outcome, information representing a medical action or an outcome to be implemented in the clinical pathway (target conditions of patient to be achieved in a particular period) is set. Examples of the information representing medical actions include observation, medication, examination, treatment, order, nutrition, and contents of description that are generally included in the clinical pathway. In the scheduled date of implementation, a scheduled date at which assessment of the medical action or the outcome will be implemented is set. The scheduled date of implementation may be in units of time.

FIG. 3 is a diagram illustrating an example of patient data obtained by the obtaining function 151 according to the first embodiment.

For example, as illustrated in FIG. 3, the patient data includes a patient code, a pathway code, the sex, the age, and a disease name as data items. In the patient code, a code for uniquely identifying a patient is set. In the pathway code, a code for uniquely identifying a clinical pathway (same content as pathway code illustrated in FIG. 2) is set. In the sex, the sex of the patient is set. In the disease name, the name of a disease of the patient is set. The patient data may include, in addition to the information described above, other information that have been determined at the time of starting the application of the clinical pathway, such as the height, weight, history of hospitalization, and allergies of the patient.

FIG. 4 is a diagram illustrating an example of historic data obtained by the obtaining function 151 according to the first embodiment.

For example, as illustrated in FIG. 4, the historic data includes a patient code, a medical action/outcome, an item, a result, and a date of implementation as data items. In the historic data, the medical action/outcome, the item, the result, and the date of implementation are each set in association with the patient code.

In the patient code, a code for uniquely identifying a patient is set (same content as patient code illustrated in FIG. 3). In the medical action/outcome, information representing a medical action or an outcome that has been implemented on the patient is set (same content as medical action/outcome illustrated in FIG. 2). In the item, an item obtained by the assessment of the medical action or the outcome is set. In the result, a result obtained by the assessment of the medical action or the outcome is set. In the result, in addition to the implementation result (implemented/unimplemented) of the medical action, data (such as food intake (%) and body temperature (degrees)) obtained as a result of the medical action is set. In the result, an assessment result (achieved/unachieved) of the outcome is set. In the date of implementation, the date of implementation at which the medical action or the outcome was assessed is set.

FIG. 5 is a diagram illustrating an example of variance data obtained by the obtaining function 151 according to the first embodiment.

For example, as illustrated FIG. 5, the variance data includes a patient code, a medical action/outcome, a variance code, a detailed variance, and the date of occurrence as data items. In the variance data, the medical action/outcome, the variance code, the detailed variance, and the date of occurrence are each set in association with the patient code.

In the patient code, a code for uniquely identifying a patient is set (same content as patient code illustrated in FIG. 3). In the medical action/outcome, information representing a medical action or an outcome that has been implemented on the patient is set (same content as medical action/outcome illustrated in FIG. 2). In the variance code, a code related to the cause of the occurrence of variance is set. In the detailed variance, information representing details of variance that has occurred in the clinical pathway is set. For example, in the detailed variance, text information describing detailed contents of the variance is set. In the date of occurrence, the date of occurrence at which the variance occurred is set.

FIG. 6 is a diagram illustrating an example of variance code master data obtained by the obtaining function 151 according to the first embodiment.

For example, as illustrated in FIG. 6, the variance code master data includes a variance code, a large category, and a variance category as data items. In the variance code, a code related to the cause of the occurrence of variance is set (same contents as variance code illustrated in FIG. 5). In the large category, a large category (such as patient factor, staff factor, facility factor, and social factor) of the cause of the occurrence of the variance is set. In the variance category, a small category (such as physical factor, patient's intention or will, and order from doctor) of the cause of the occurrence of the variance is set.

Referring back to FIG. 1, the extracting function 152 extracts, based on data on medical actions implemented in accordance with a clinical pathway and data on variance generated in the clinical pathway, relevant factors associated with the variance.

Specifically, the extracting function 152 uses information on patient data, historic data, and variance data stored in the storage 120 as information representing relevant factors associated with the variance to extract an association rule that is a combination of elements associated with the variance. As a method for generating the association rule, various kinds of publicly known analysis methods can be used.

In the first embodiment, the extracting function 152 generates association rules by using association analysis on the assumption that sets of association rules and numerical values representing the degree of correlation are obtained. The extracting function 152 may use sequential association analysis or sequential pattern mining, which is association analysis taking the order of occurrence into consideration.

The association analysis is the task of extracting a rule "Y happens under the condition X", where X represents an item serving as the antecedent and Y represents an item serving as the consequent. In general, rules are evaluated by using the support, the confidence, and the lift defined as follows as index values.

$$\text{Support } (x \Rightarrow Y) = \frac{n(X \cap Y)}{n(A)} \tag{1}$$

$$\text{Confidence } (X \Rightarrow Y) = \frac{n(X \cap Y)}{n(X)} \tag{2}$$

-continued $$\text{Lift}(X \Rightarrow Y) = \frac{\text{Confidence}(X \Rightarrow Y)}{n(Y)/n(A)} \quad (3)$$

where n(X) is the number of transactions including X, n(Y) is the number of transactions including Y, n(X∩Y) is the number of transactions including both X and Y, and n(A) is the total number of transactions.

In the first embodiment, the extracting function 152 performs association analysis by using a set of data on medical actions/outcomes that have occurred from the start to the end of a clinical pathway, data on variance that has occurred from the start to the end of the clinical pathway, and data on a patient to which the clinical pathway is applied as a transaction.

Specifically, the extracting function 152 receives, from the operator through the input circuitry 130, an operation of designating a clinical pathway. The extracting function 152 refers to patient data to specify data on a patient to which the clinical pathway designated by the operator is applied. The extracting function 152 refers to historic data to specify, for each specified patient, data on medical actions or outcomes implemented on the patient. Furthermore, the extracting function 152 refers to the variance data to specify, for each specified patient, data on variance generated by medical actions implemented on each patient. The extracting function 152 generates a corresponding set of data on the medical action/outcome, data on the variance, and data on the patient as a transaction.

In the association analysis, each item needs to be qualitative data, and hence data having numerical data is converted into qualitative data. For example, each item is converted into a label on nominal scale, such as "SOLDEM 3A 500 ml (1, implemented as planned)" in the case where the infusion of 500 ml of SOLDEM 3A was implemented on day 1 as planned by the clinical pathway, "SOLDEM 3A 500 ml (1, unimplemented)" in the case where the infusion was not implemented as planned, and "BFLUID 100 ml (2, not implemented as planned)" in the case where an item that is not included in the clinical pathway was implemented. The brackets mean (date of implementation or date of occurrence, relation with clinical pathway). The nominal scale may be divided into stages. Dates of implementation or dates of occurrence may be collectively converted into one label.

The extracting function 152 uses each of the generated transactions to generate an association rule in which data on the medical action/outcome is the antecedent and data on the variance is the consequent, and calculates the support, the confidence, and the lift for the generated association rule. The extracting function 152 generates association rule data in which the association rule and each index value are associated with each other, and stores the association rule data in the storage 120.

FIG. 7 is a diagram illustrating an example of association rule data generated by the extracting function 152 according to the first embodiment.

For example, as illustrated in FIG. 7, the association rule data includes an antecedent, a consequent, a support, a confidence, and a lift as data items. In the antecedent, data on a medical action/outcome is set. In the consequent, data on variance is set. In the support, the confidence, and the lift, the values of the support, the confidence, and the lift calculated by the extracting function 152 are set, respectively.

FIG. 7 illustrates an example of association rule data generated when association analysis is performed on variance of "anastomotic leakage". Symbol "+" included in the antecedent illustrated in FIG. 7 represents a combination of medical actions or outcomes that have occurred at the same time.

In this manner, in the association rule data, the consequent represents variance, and the antecedent represents relevant factors associated with the variance. The support, the confidence, and the lift are correlation values representing the degree of correlation between each relevant factor and the variance.

Referring back to FIG. 1, the classifying function 153 allocates elements included in classification criteria to the relevant factors extracted by the extracting function 152, thereby classifying the relevant factors. The classification criteria are criteria for classification to characterize the clinical pathway, and include one or more elements.

Specifically, the classification criteria are defined based on at least one of the purpose of analysis, time, medical care cost, complexity of the relevant factors, order type, and the relation with a pathway item in a clinical pathway. Here, the pathway item is, for example, an item of a medical care plan or medical care flow. For example, classification criteria based on the purpose of analysis include pre-detection, preventive measure, and review on exclusion criteria as elements of the classification criteria. Classification criteria based on time include a phase in a clinical pathway and a day relative to a surgery day as elements of the classification criteria. Classification criteria based on medical care cost include fee-for-service medical points as an element of the classification criteria. Classification criteria based on the complexity of the relevant factors include the number of antecedents and the number of types of order attributes as elements of the classification criteria. Classification criteria based on the order type include examination, medication, treatment, nutrition, observation, and advice as elements of the classification criteria. Classification criteria based on the relation with pathway items in the clinical pathway include criteria that elements other than a pathway item are included and criteria that only a pathway item is included as elements of the classification criteria.

In the first embodiment, the classifying function 153 classifies relevant factors by referring to classification criterion master data, classification master data, and transition rule master data stored in the storage 120 in advance. The classification criterion master data is data defining classification criteria and elements thereof. The classification master data is data that defines association between a relevant factor and an element of classification criteria. The transition rule master data is data that defines constraints (transition rule) on transition between classification criteria when relevant factors are refined in a stepwise manner based on classification criteria.

FIG. 8 is a diagram illustrating an example of classification criterion master data used by the classifying function 153 according to the first embodiment.

For example, as illustrated in FIG. 8, the classification criterion master data is data in which information indicating classification criteria and information indicating elements included in the classification criteria are associated with each other. For example, the information indicating classification criteria includes a classification criterion code for identifying a classification criterion and the name of the classification criterion. The information indicating elements included in the classification criteria includes an element code for identifying an element and the name of the element.

For example, in the example illustrated in FIG. 8, the classification criterion master data illustrated on the upper left defines that "purpose classification" (classification criterion code: A) serving as a classification criterion based on the purpose of analysis includes "pre-detection" (element code: A-1), "preventive measure" (element code: A-2), and "review on exclusion criteria" (element code: A-3) as elements.

FIG. 9 is a diagram illustrating an example of classification master data used by the classifying function 153 according to the first embodiment.

For example, as illustrated in FIG. 9, the classification master data is data in which an item label included in an association rule and element codes of classification criteria are associated with each other. The item label in the association rule is associated with one or more element code for each classification criterion. For example, some classification criteria such as "number of antecedents" (classification criterion code: H) illustrated in FIG. 8 are classification criteria for an association rule that is a combination of item labels, and hence classification master data is not set to such classification criteria.

For example, in the example illustrated in FIG. 9, the classification master data in the first row defines that an item label of "abnormal PCT value" included in the association rule is associated with "pre-detection" (element code: A-1), which is an element of "purpose classification" (classification criterion code: A), "intermediate" (element code: B-2), which is an element of "medical care cost" (classification criterion code: B), "examination" (element code: C-1), which is an element of "order type large category" (classification criterion code: C), "sampling" (element code: D-1), which is an element of "order type small category (classification criterion code: D), "postoperative days 4 to 6" (element code: E-4), which is an element of "phase" (classification criterion code: E), and " . . . " (element code: F-7), which is an element of "phase (date)" (classification criterion code: F).

FIG. 10 is a diagram illustrating an example of transition rule master data used by the classifying function 153 according to the first embodiment.

For example, as illustrated in FIG. 10, the transition rule master data is data in which selected classifications or elements are associated with selectable classifications or elements and unselectable classifications or elements. The transition rule master data is set in accordance with the dependency relation among classification criteria.

In the "selected classification or element", information (such as classification criterion code or element code) representing one classification criterion or element among classification criteria or elements having dependency relation is set. In the "selectable classification or element", information (such as classification criterion code or element code) representing a classification criterion or element serving as a subclassification (classification of narrower concept) of the classification criterion or element set in the "selected classification or element" is set. In the "unselectable classification or element", information (such as classification criterion code or element code) representing a classification criterion or element serving as a dominant classification (classification of broader concept) of the classification criterion or element set in the "selected classification or element" is set.

For example, the example illustrated in FIG. 10 indicates that, when an element included in the "order type large category" (classification criterion code: C) is selected, elements in the "order type small category" (classification criterion code: D) and the "number of large category types" (classification criterion code: I) serving as a narrower concept of the order type can be selected, but elements in the "purpose classification" serving as a dominant concept of the order type cannot be selected.

FIG. 11 is a diagram illustrating an example of transition of classification criteria defined by transition rule master data according to the first embodiment.

For example, as illustrated in FIG. 11, when "high" (element code: B-3), which is an element in "medical care cost" (classification criterion code: B), is selected from among "purpose classification" (classification criterion code: A), "medical care cost" (classification criterion code: B), "order type large category" (classification criterion code: C), "phase" (classification criterion code: E), "number of antecedents" (classification criterion code: H), and "relation with pathway item" (classification criterion code: K), a transition rule that enables only "purpose classification" (classification criterion code: A), "order type large category" (classification criterion code: C), "phase" (classification criterion code: E), "number of antecedents" (classification criterion code: H), and "relation with pathway item" (classification criterion code: K) to be selected is defined by transition rule master data.

Specifically, the classifying function 153 refers to the above-mentioned classification criterion master data, classification master data, and transition rule master data to classify association rule data that is information representing relevant factors.

First, the classifying function 153 allocates association rule data generated by the extracting function 152 an element in classification criteria associated with each item label in the classification master data based on each item label included in the antecedent in the association rule data.

When the number of item labels included in the antecedent in the association rule data is one, the classifying function 153 allocates, for each classification criterion, an element associated with the item label in the classification master data to the association rule data. When the number of item labels included in the antecedent in the association rule data is two or more, the classifying function 153 employs, for each classification criterion, an element common to elements associated with the item labels in the classification master data, and allocates the element to the association rule data.

FIG. 12 is a diagram illustrating an example of allocation of elements in classification criteria performed by the classifying function 153 according to the first embodiment. FIG. 12 illustrates an example where the classification criterion master data illustrated in FIG. 8 and the classification master data illustrated in FIG. 9 are used to allocate elements in classification criteria.

For example, as indicated by "abnormal PCT value+ abnormal abdominal pain" in FIG. 12, when "abnormal PCT value" and "abnormal abdominal pain" are included in the antecedent in the association rule data, the classifying function 153 allocates "pre-detection" (element code: A-1), which is common to "abnormal PCT value" and "abnormal abdominal pain", to an item label set for the antecedent in the association rule data as an element for "purpose classification" (classification criterion code: A) (see FIG. 9).

For "order type large category" (classification criterion code: C), on the other hand, "abnormal PCT value" is associated with "examination" (element code: C-1) and "abnormal abdominal pain" is associated with "observation"

(element code: C-5) (see FIG. 9). Thus, the classifying function 153 does not allocate elements because there is no common element.

For example, when the number of item labels included in the antecedent in the association rule data is two or more, the classifying function 153 may employ all elements associated with at least one item label, rather than employing a common element associated with the item labels. In this case, for example, in the above-mentioned example, the classifying function 153 allocates both of "examination" (element code: C-1) and "observation" (element code: C-5) to item labels ("abnormal PCT value" and "abnormal abdominal pain") set to the antecedent in the association rule data as elements of "order type large category" (classification criterion code: C).

In regard to classification criteria for association rules, that are not set in the classification master table, the classifying function 153 allocates elements based on association rule conditions. For example, the classifying function 153 allocates an element to "number of antecedents" (classification criterion code: H) (see FIG. 8) based on the number of item labels included in the antecedent in the association rule data. For example, in the above-mentioned example, the number of item labels ("abnormal PCT value" and "abnormal abdominal pain") included in the antecedent in the association rule data is two, and hence the classifying function 153 allocates "2 to 3" (element code: H-2) as "number of antecedents" (classification criterion code: H) (see FIG. 8).

After that, the classifying function 153 classifies the association rule data based on elements of classification criteria allocated to each association rule data. Each time the display controlling function 155 described later receives an operation of designating classification criteria from the operator, the classifying function 153 classifies association rule data in regard to all selectable classification criteria defined in the transition rule master data for each element included in the designated classification criteria.

Specifically, the classifying function 153 generates association rule classification data obtained by aggregating association rules allocated with the same element based on elements in classification criteria allocated to each association rule data.

FIG. 13 is a diagram illustrating an example of classification of association rule data performed by the classifying function 153 according to the first embodiment. FIG. 13 illustrates an example where association rule data is classified based on elements of "purpose classification" (classification criterion code: A).

For example, as indicated on the upper stage in FIG. 13, the classifying function 153 generates association rule classification data obtained by aggregating association rule data allocated with "pre-detection" (element code: A-1) for "purpose classification" (classification criterion code: A). For example, as indicated on the middle stage in FIG. 13, the classifying function 153 generates association rule classification data obtained by aggregating association rule data allocated with "preventive measure" (element code: A-2) for "purpose classification" (classification criterion code: A). For example, as indicated on the bottom stage in FIG. 13, the classifying function 153 generates association rule classification data obtained by aggregating association rule data allocated with "review on exclusion criteria" (element code: A-3).

For all selectable classification criteria defined in the transition rule master data, the classifying function 153 generates association rule classification data for each element included in the classification criteria similarly to the above-mentioned example.

Referring back to FIG. 1, the aggregating function 154 aggregates relevant factors for each classification criterion that characterizes a clinical pathway. The aggregating function 154 aggregates relevant factors classified by the classifying function 153 for each element in classification criteria.

Specifically, the aggregating function 154 aggregates, for each element in classification criteria, association rule classification data generated by the classifying function 153, and extracts characteristics of an association rule. For example, as the characteristics of the association rule, the aggregating function 154 extracts a distribution (histogram) of the confidence, a maximum value of the confidence, and an association rule having the maximum confidence.

FIG. 14 is a diagram illustrating an example of the result of extracting characteristics in an association rule extracted by the aggregating function 154 according to the first embodiment. FIG. 14 illustrates an example of the result of extracting characteristics in an association rule for elements of "purpose classification" (classification criterion code: A).

For example, as illustrated in FIG. 14, the aggregating function 154 extracts the distribution (histogram) of the confidence, the maximum value of the confidence, and an association rule (relevant factors) having the maximum confidence for each of "pre-detection" (element code: A-1), "preventive measure" (element code: A-2), and "review on exclusion criteria" (element code: A-3) included in "purpose classification" (classification criterion code: A).

For example, the example illustrated in FIG. 14 indicates that the confidence of an association rule (relevant factors) of "abnormal PCT value+abnormal abdominal pain+anastomotic leakage" is maximum and the confidence is "90%" for "pre-detection" (element code: A-1). The example illustrated in FIG. 14 also indicates that the confidence of an association rule (relevant factors) of "preoperative fasting+anastomotic leakage" is maximum and the confidence is "75%" for "preventive measure" (element code: A-2). The example illustrated in FIG. 14 also indicates that the confidence of an association rule (relevant factors) of "under the age of 65+abdominal surgery+anastomotic leakage" is maximum and the confidence is "43%" for "review on exclusion criteria" (element code: A-3).

While an example where the aggregating function 154 uses the confidence as an assessment index for an association rule has been described, the embodiments are not limited thereto. For example, the aggregating function 154 may use other indices such as the support and the lift, or may use an index calculated by a combination of indices.

Referring back to FIG. 1, the display controlling function 155 displays relevant factors aggregated by the aggregating function 154 on the display 140 for each classification criterion.

Specifically, the display controlling function 155 generates, for each element of classification criteria, information representing characteristics of an association rule extracted by the aggregating function 154 as an aggregation result, and displays an analysis result screen on which the generated aggregation results are arranged side by side and displayed on the display 140.

Figure 15:
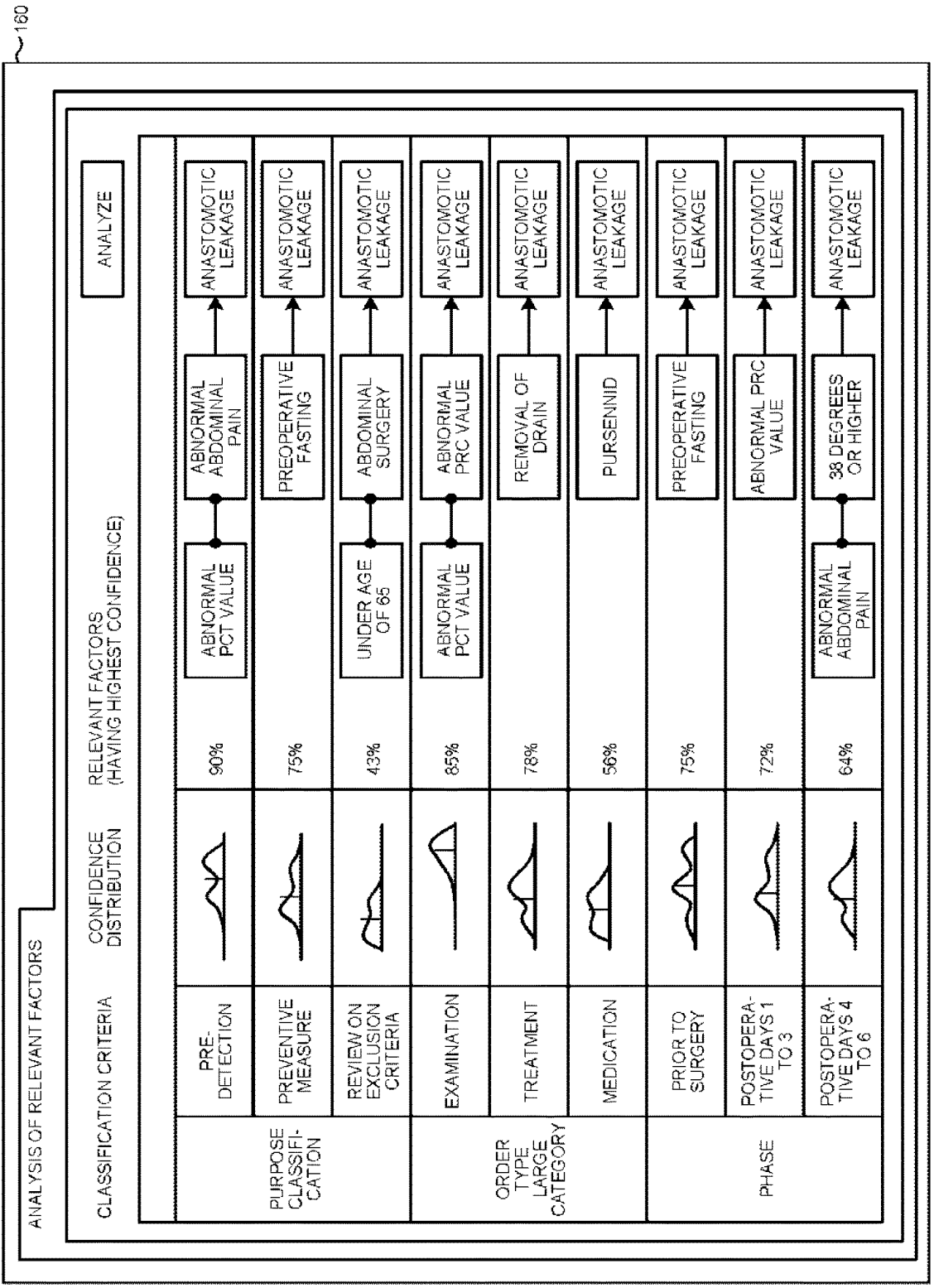
FIG. 15 is a diagram illustrating an example of an analysis result screen displayed by a display controlling function according to the first embodiment.
Figure 16:
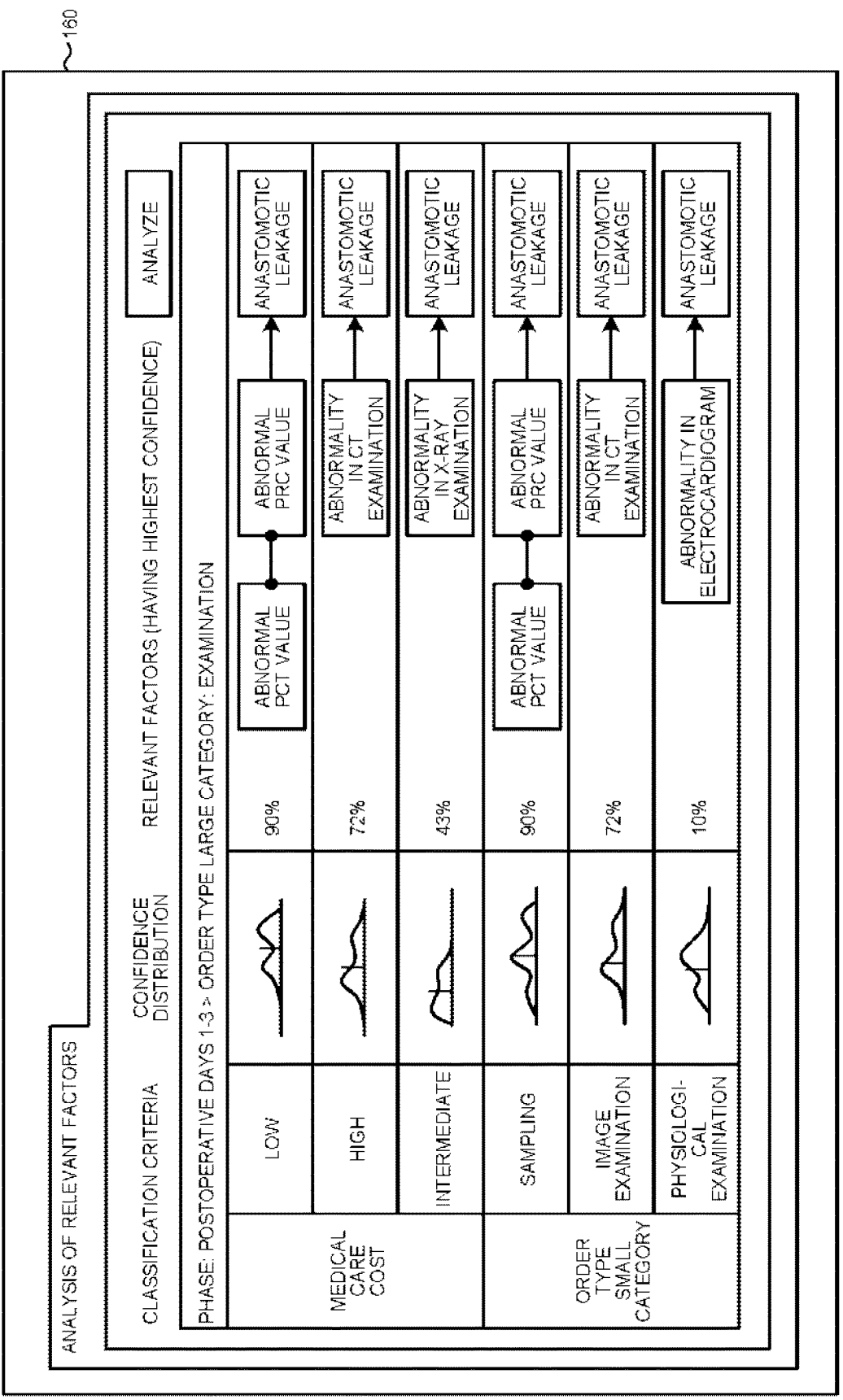
FIG. 16 is a diagram illustrating an example of the analysis result screen displayed by the display controlling function according to the first embodiment.

FIGS. 15 and 16 are diagrams illustrating examples of an analysis result screen displayed by the display controlling function 155 according to the first embodiment.

For example, as illustrated in FIG. 15, the display controlling function 155 generates an analysis result screen 160 in which pieces of information, in each of which an element in classification criteria and its aggregation result are horizontally arranged, are vertically arranged for each element in the classification criteria, and displays the generated analysis result screen 160 on the display 140. In this manner, the aggregation results of the elements in the classification criteria are arranged side by side and displayed, which enables the operator to easily compare the distributions of association rules included in classification criteria among classification criteria.

The display controlling function 155 further receives, from the operator through the input circuitry 130, an operation of designating one element from among elements of classification criteria displayed on the analysis result screen 160. When an element of the classification criteria is designated by the operator, the display controlling function 155 displays, instead of the aggregation results that have been displayed so far, aggregation results of elements included in classification criteria that are subclassifications of the designated element of classification criteria in transition rule master data on the analysis result screen 160.

For example, FIG. 16 illustrates an example where "postoperative days 1 to 3" (element code: E-3) included in "phase" (classification criterion code: E) is designated and "examination" (element code: C-1) included in "order type large category" (classification criterion code: C) is thereafter designated. In this manner, each time new classification criteria are designated by an operator, the display controlling function 155 changes aggregation results displayed on the analysis result screen 160 based on the designated classification criteria.

Each of the processing functions in the processing circuitry 150 has been described above. For example, each of the above-mentioned processing functions is stored in the storage 120 in the form of a computer program that can be executed by a computer. The processing circuitry 150 reads each of the computer programs from the storage 120, and executes each of the read computer programs, thereby implementing the processing function corresponding to each of the computer programs. In other words, the processing circuitry 150 that has read each of the computer programs has each of the processing functions illustrated in FIG. 1.

While an example where each of the above-mentioned processing functions is implemented by the single processing circuitry 150 has been described with reference to FIG. 1, the embodiments are not limited thereto. For example, the processing circuitry 150 may be configured by a combination of independent processors, and each processor may implement each processing function by executing each computer program. The processing functions in the processing circuitry 150 may be implemented by being appropriately dispersed or integrated into a single or plurality of processing circuitries.

The term "processor" used in the above description means, for example, a central processing unit (CPU), a graphics processing unit (GPU), or a circuit such as an application specific integrated circuit (ASIC), a programmable logic device (for example, a simple programmable logic device (SPLD), a complex programmable logic device (CPLD), and a field programmable gate array (FPGA)). The processor implements functions by reading and executing a computer program stored in the storage 120. Instead of storing a computer program in the storage 120, a computer program may be configured to be directly embedded in a circuit of the processor. In this case, the processor implements functions by reading and executing a computer program embedded in the circuit. Each processor in the first embodiment is not limited to the case where each processor is configured as a single circuit, and independent circuits may be combined to configure a single processor so as to implement their functions.

A computer program to be executed by the processor is provided by being embedded in a read only memory (ROM) or a storage in advance. The computer program may be provided by being recorded in a storage medium that can be read by a computer, such as a compact disc (CD)-ROM, a flexible disk (FD), a CD recordable (CD-R), and a digital versatile disc (DVD), as a file in the form that can be installed or executed by the apparatus. The computer program may be stored on a computer connected to a network such as the Internet, and provided or distributed by being downloaded via the network. For example, the computer program is configured by a module including each functional unit described later. As hardware in practice, a CPU reads and executes a computer program from a storage medium such as a ROM, so that each module is loaded on a main storage device and created on the main storage device.

Figure 17:
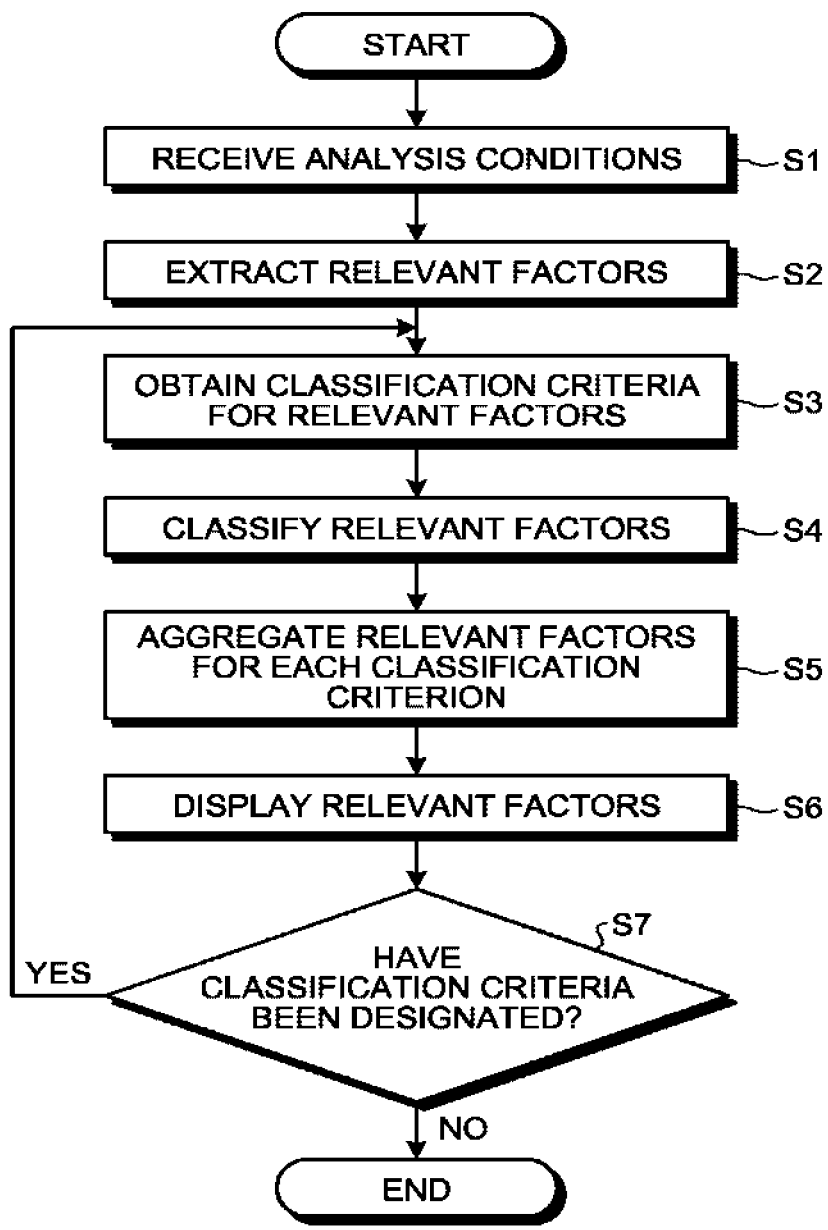
FIG. 17 is a flowchart illustrating a processing procedure of processing performed by the medical information processing apparatus according to the first embodiment.

FIG. 17 is a flowchart illustrating a processing procedure of processing performed by the medical information processing apparatus 100 according to the first embodiment. Processing in which the obtaining function 151 obtains data on medical actions implemented in accordance with a clinical pathway and data on variance generated in the clinical pathway is performed asynchronously with the processing procedure described below. For example, the processing performed by the obtaining function 151 is implemented by the processing circuitry 150 reading a predetermined computer program corresponding to the obtaining function 151 from the storage 120 and executing the read computer program.

For example, as illustrated in FIG. 17, in the first embodiment, the extracting function 152 receives analysis conditions (clinical pathway) from an operator (Step S1). After that, based on data on medical actions implemented in accordance with the clinical pathway designated by the operator and data on variance generated in the clinical pathway, the extracting function 152 extracts relevant factors associated with the variance (Step S2).

Subsequently, the classifying function 153 obtains relevant factor classification criteria designated by the operator (Step S3). The classifying function 153 classifies the relevant factors for each element included in the designated classification criteria (Step S4).

After that, the aggregating function 154 aggregates the relevant factors classified by the classifying function 153 for each element in the classification criteria (Step S5).

The display controlling function 155 displays the relevant factors aggregated by the aggregating function 154 on the display 140 for each classification criterion (Step S6).

When new classification criteria are designated by the operator (Yes at Step S7), the flow returns to Step S3, and the processing procedure of Steps S3 to S6 is executed again. When classification criteria are not designated by the operator (No at Step S7), the processing is finished.

Steps S1 and S2 described above are implemented by, for example, the processing circuitry 150 reading a predetermined computer program corresponding to the extracting function 152 from the storage 120 and executing the read computer program. Steps S3 and S4 are implemented by, for example, the processing circuitry 150 reading a predetermined computer program corresponding to the classifying function 153 from the storage 120 and executing the read computer program. Step S5 is implemented by, for example, the processing circuitry 150 reading a predetermined computer program corresponding to the aggregating function 154 from the storage 120 and executing the read computer program. Step S6 is implemented by, for example, the processing circuitry 150 reading a predetermined computer program corresponding to the display controlling function 155 from the storage 120 and executing the read computer program.

As described above, in the first embodiment, based on data on medical actions and data on variance, the extracting function 152 extracts relevant factors associated with the variance. The classifying function 153 classifies the relevant factors by allocating elements included in classification criteria that characterize a clinical pathway to the relevant factors, and the display controlling function 155 displays the aggregated relevant factors on the display 140 for each classification criterion. Consequently, according to the first embodiment, the causes of variance can be effectively refined and presented.

For example, in some of the related art, when association rule mining is used to analyze the cause of variance in detail, hierarchical order attributes are used to abstract association rules to refine and extract effective association rules in a stepwise manner from massive association rules. Such related art, however, cannot always efficiently analyze the variance.

In general, in variance analysis, an effective refining method is different depending on its analysis purpose and what is emphasized. For example, variance of anastomotic leakage in a surgery may be analyzed in regard to different purposes of preventive measure and pre-detection of anastomotic leakage in some cases, the cause of the variance may be analyzed by limiting to a particular phase in a clinical pathway, or tasks with large medical care cost may be analyzed with priority. The analysis purpose is not always definite from the beginning, and the analysis purpose may be determined while comparing the degree of correlation with variance from various viewpoints. In regard to this, the above-mentioned related art assumes that the division pattern of the hierarchical structure of attributes is single, and hence only the granularity is taken into account in the refinement, and refinement suitable for the user purpose cannot be achieved. Refinement while comparing the correlation with variance from various viewpoints cannot be achieved.

Unlike the related art, in the above-mentioned embodiment, the causes of variance are effectively refined and presented for each classification criterion that characterizes a clinical pathway, and hence the variance can be efficiently analyzed.

Second Embodiment

In the above-mentioned embodiment, an example where the display controlling function 155 changes aggregation results displayed on the analysis result screen 160 based on designated classification criteria each time new classification criteria are designated by an operator has been described, but the embodiments are not limited thereto.

In the following, as a second embodiment, an example where the display controlling function 155 refines classification criteria based on analysis conditions designated by an operator, and displays relevant factors for each of the refined classification criteria is described. In the second embodiment, differences from the above-mentioned embodiment are mainly described, and descriptions of contents overlapping with the above-mentioned embodiment are omitted.

For example, the display controlling function 155 displays a graphical user interface (GUI) for receiving analysis conditions from an operator on an analysis result screen for displaying aggregation results of association rules. The display controlling function 155 refines classification criteria in accordance with the analysis conditions received through the GUI, and displays the aggregation results of association rules for each of the refined classification criteria.

Figure 18:
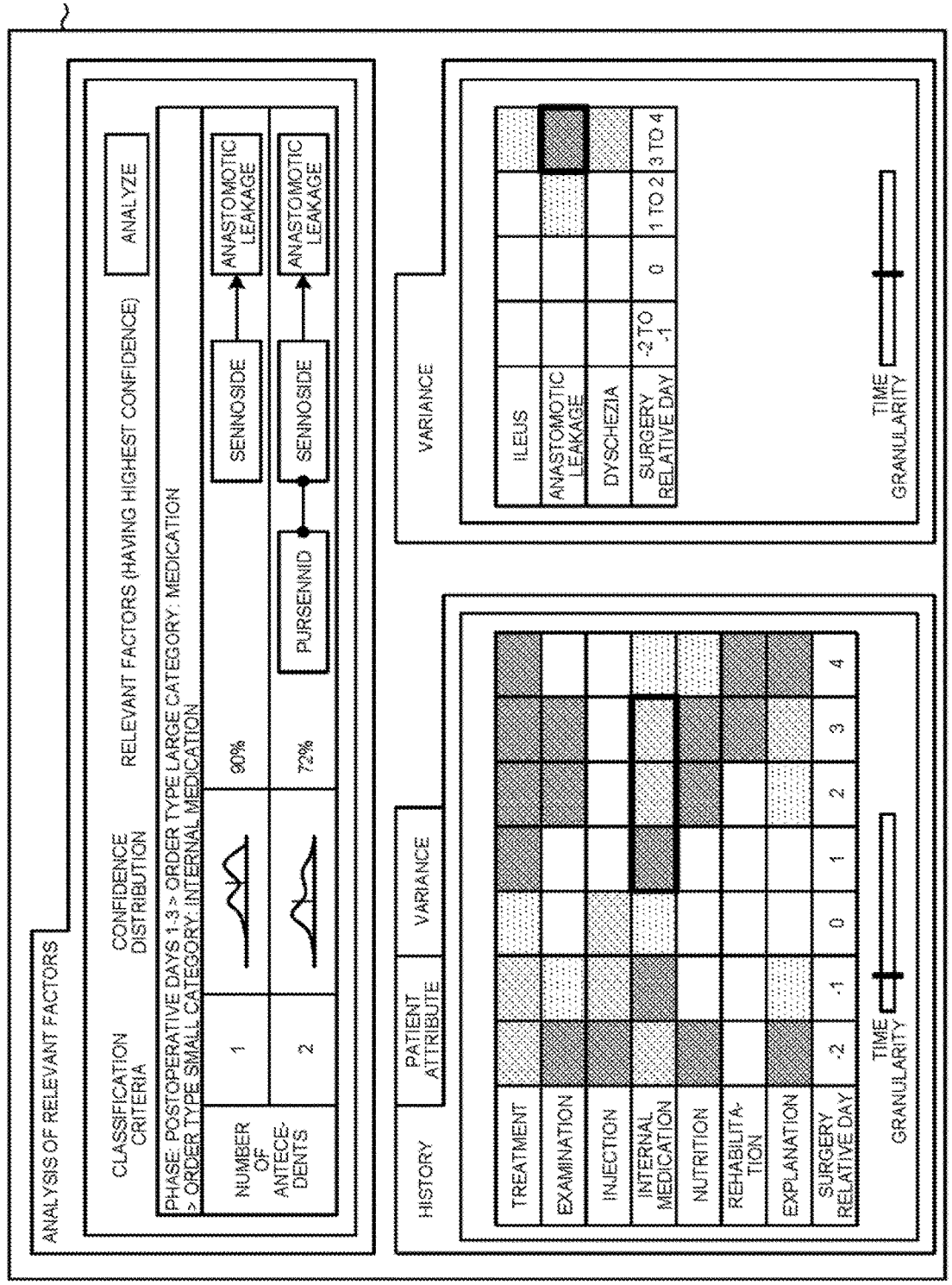
FIG. 18 is a diagram illustrating an example of an analysis result screen displayed by a display controlling function according to a second embodiment.

FIG. 18 is a diagram illustrating an example of an analysis result screen displayed by the display controlling function 155 according to the second embodiment.

For example, as illustrated in FIG. 18, the display controlling function 155 displays, on the display 140, an analysis result screen 260 on which information in which elements of classification criteria and aggregation results thereof are horizontally arranged side by side is arranged side by side in the vertical direction for each element of the classification criteria on an upper part of the screen, and two panels for receiving analysis conditions are arranged on the left and right on a lower part of the screen.

Two panels are arranged on the left and right on the lower part of the screen such that the left panel is used to designate items included in the antecedent (history, patient attributes, variance) of an association rule and the right panel is used to designate items included in the consequent (variance) of the association rule. Each panel includes areas sectioned by time and type. The display controlling function 155 receives through the input circuitry 130 an operation of selecting an area on each panel, thereby receiving a designation of items serving as analysis conditions from the operator. A slider disposed on the lower part of each panel is used to receive from the operator an operation of adjusting the granularity of time for sectioning the areas.

In this case, for example, the display controlling function 155 displays the proportion of the number of data including particular items to the number of historic data, patient data, or variance data in individual areas included in each panel with use of density of color. For example, the display controlling function 155 displays areas included in a panel for history such that color becomes darker as the proportion of data in which the implementation result was "implemented" on a corresponding surgery relative day (day relative to surgery day) is larger in historic data. For example, the display controlling function 155 displays areas included in a panel for variance such that color becomes darker as the proportion of variance that has occurred on a corresponding surgery relative day is larger in variance data.

When only data on patients to which clinical pathways are applied has been obtained by the obtaining function 151, the display controlling function 155 calculates the proportion of the number of data including particular items based on the data on patients to which clinical pathways are applied, and determines the degree of density of color in each area. On the other hand, when both data on patients to which clinical pathways are applied and data on patients to which clinical pathways are not applied have been obtained by the obtaining function 151, the display controlling function 155 calculates the proportion of the number of data including particular items based on the data on all patients, and determines the degree of density of color in each area.

FIG. 18 illustrates an example where internal medication implemented on surgery relative days 1 to 3 and variance of anastomotic leakage that has occurred on surgery relative days 3 and 4 are designated by an operator. In this case, the display controlling function 155 determines that this state is equal to the case where "postoperative days 1 to 3" (element code: E-3) included in "phase" (classification criterion code: E) is designated by the operator and thereafter "internal medication" included in "order type small category" (classification criterion code: D) is designated by the operator. The display controlling function 155 refines the classification criteria, and displays aggregation results of association rules for each of the refined classification criteria.

In this manner, in the second embodiment, the display controlling function 155 presents classification criteria such that the classification criteria are refined from the beginning based on analysis conditions designated by the operator. Here, the display controlling function 155 displays, on the display 140, first information (area) associating a type and implementation timing of the medical action for each of types and implementation timings of the medical action. Further, the display controlling function 155 displays, on the display 140, second information (area) associating a type and occurrence timing of the variance for each of types and occurrence timings of the variance. Then, the display controlling function 155 receives, from an operator, an operation selecting at least one combination of the first and second information as the analysis conditions from the displayed first and second information, and refines the classification criteria by selecting classification criteria corresponding to the at least one combination. Here, the display controlling function 155 emphatically displays first information indicating a type and implementation timing of a medical action implemented frequently and second information indicating a variance occurred frequently.

Consequently, according to the second embodiment, the operator can effectively reach desired refining conditions.

Third Embodiment

In the above-mentioned embodiments, an example where the display controlling function 155 displays relevant factors on the analysis result screen as an aggregation result such that the relevant factors are arranged side by side in the vertical direction has been described, but when the number of the relevant factors to be displayed is large, the relevant factors may be displayed outside an initial display range on the analysis result screen.

Thus, in the following, as a third embodiment, an example where the display controlling function 155 determines the display order of the relevant factors in accordance with a correlation value representing the degree of correlation between the relevant factors and variance or a distribution of the correlation value is described. In the third embodiment, differences from the above-mentioned embodiments are mainly described, and descriptions of contents overlapping with the above-mentioned embodiments are omitted.

For example, the display controlling function 155 rearranges classification criteria to be displayed and their elements based on a distribution of an index of an association rule included in each element of the classification criteria. For example, the display controlling function 155 rearranges the elements of the classification criteria such that an element in which the maximum value, average value, or kurtosis of the confidence is large or the number of association rules included in the element is large is disposed on the upper side. For example, the display controlling function 155 rearranges the classification criteria such that classification criteria in which the average value of a predetermined number of confidences having larger confidence values is large or a variation in distribution of confidences among elements (difference or variance of average values of confidences among elements) is large is disposed on the upper side. That is, the display controlling function 155 determines the display order of the relevant factors so that a relevant factor of which the correlation value is larger is displayed on the upper side for each of the classification criteria. In this manner, important classification criteria and association rules are displayed on the upper side to enable a burden for an operator to search for classification criteria and association rules to be eliminated and prevent an effective association rule from being disposed outside an initial display range on the analysis result screen.

As described above, in the third embodiment, the display controlling function 155 determines the display order of the relevant factors in accordance with a correlation value representing the degree of correlation between the relevant factors and the variance or a distribution of the correlation value. Consequently, according to the third embodiment, the operator can easily recognize important relevant factors.

Fourth Embodiment

In the above-mentioned embodiments, an example where the display controlling function 155 displays relevant factors for each single classification criterion has been described, but the embodiments are not limited thereto.

In the following, as a fourth embodiment, an example where the aggregating function 154 aggregates relevant factors for each first classification criterion, and thereafter further aggregates the aggregated relevant factors for each second classification criterion, which is a subclassification of the first classification criteria, and the display controlling function 155 displays the aggregated relevant factors for each second classification criterion in regard to the first classification criteria is described. In the fourth embodiment, differences from the above-mentioned embodiments are mainly described, and descriptions of contents overlapping with the above-mentioned embodiments are omitted.

Specifically, in the fourth embodiment, the classifying function 153 classifies relevant factors based on elements included in first classification criteria, and thereafter further classifies the relevant factors based on elements included in second classification criteria. The aggregating function 154 aggregates relevant factors for each element included in the second classification criteria in regard to each element of the first classification criteria, and the display controlling function 155 displays the aggregated relevant factors for each element included in the second classification criteria in regard to each element included in the first classification criteria.

Figure 19:
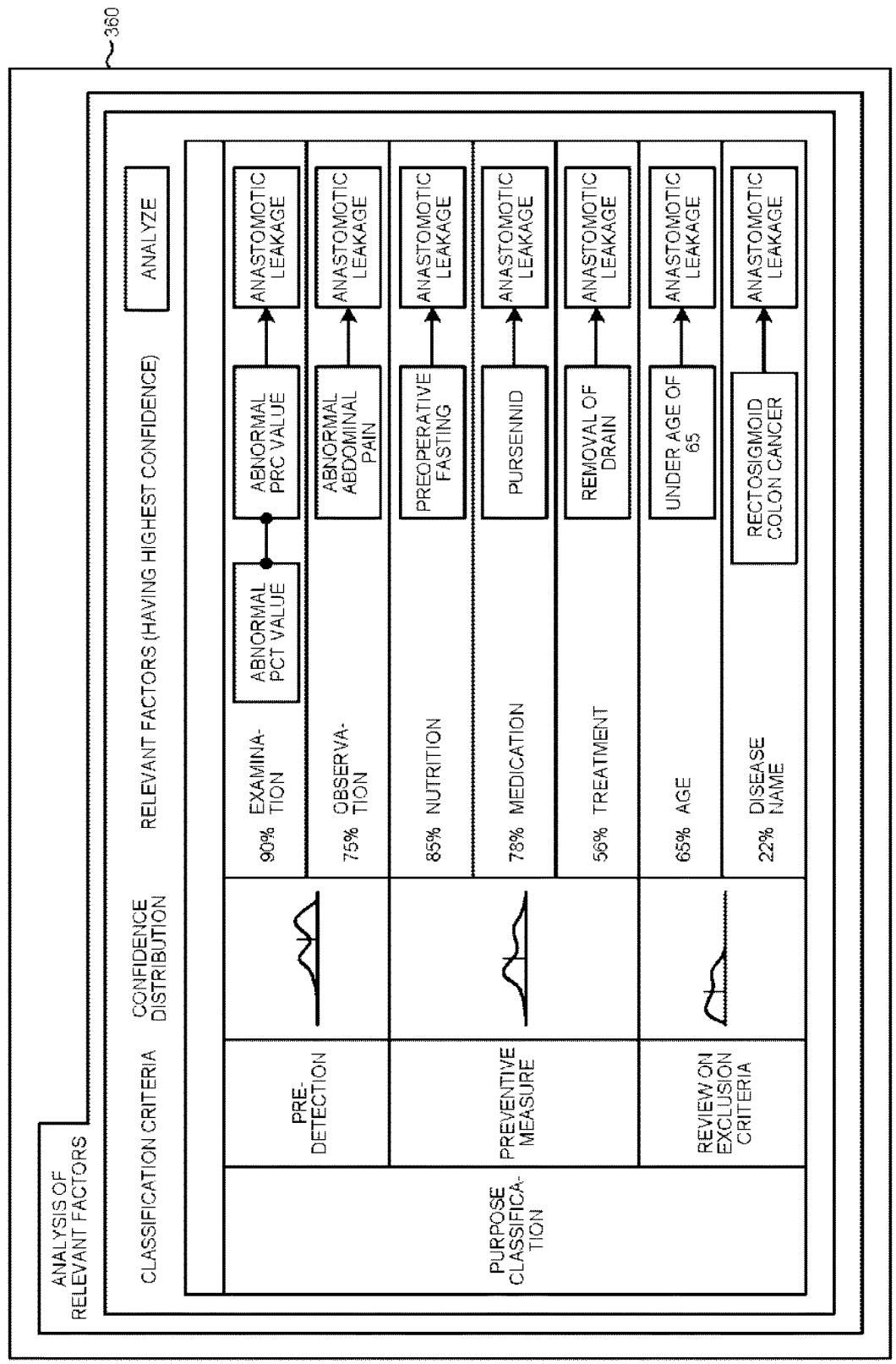
FIG. 19 is a diagram illustrating an example of an analysis result screen displayed by a display controlling function according to a fourth embodiment.

FIG. 19 is a diagram illustrating an example of an analysis result screen displayed by the display controlling function 155 according to the fourth embodiment. FIG. 19 illustrates an example where association rules (relevant factors) for elements of "purpose classification" (classification criterion code: A) are further classified and aggregated by elements of "order type large category" (classification criterion code: C), which is one of the subclassifications of the "purpose classification" (classification criterion code: A).

For example, as illustrated in FIG. 19, the display controlling function 155 displays, on an analysis result screen 360 similar to the analysis result screen 160 illustrated in FIG. 15, in regard to association rules (relevant factors) further classified and aggregated by elements of "order type large category" (classification criterion code: C), pieces of information in each of which an element of classification criteria and its aggregation result (distribution (histogram) of confidence, maximum value of confidence, and association rule having maximum confidence) are horizontally arranged, the information being vertically arranged side by side for each element of the classification criteria.

In this manner, in the fourth embodiment, the aggregating function 154 aggregates relevant factors for each first classification criterion, and thereafter further aggregates the aggregated relevant factors for each second classification criterion, which is a subclassification of the first classification criteria, and the display controlling function 155 displays the aggregated relevant factors for each second classification criterion in regard to the first classification criteria. Consequently, in the fourth embodiment, similar association rules are less likely to be displayed, and relevant factors can be easily refined in a stepwise manner.

According to at least one of the embodiments described above, causes of variance can be effectively refined and presented.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising processing circuitry configured to:
obtain first data on medical actions and second data on differences between planned medical actions or achievement objectives of treatment and results thereof;
extract, based on the first data and the second data, relevant factors that are medical actions or achievement objectives associated with the differences and produce association rule data;
classify the relevant factors into a plurality of classification criteria each including a plurality of elements to characterize the medical actions or achievement objectives, and correlate the elements to the classified relevant factors for each of the classification criteria and produce association rule classification data;
aggregate the classified relevant factors for each of the correlated elements of each of the classification criteria, thereby classifying the association rule classification data; and
display the aggregated relevant factors with the correlated elements on a display for each of the correlated elements of each of the classification criteria.

2. The medical information processing apparatus according to claim 1, wherein the classification criteria are defined based on at least one of a purpose of analysis, a time, a medical care cost, complexity of the relevant factors, order type, and a relation with an item of a medical care plan or medical care flow.

3. The medical information processing apparatus according to claim 1, wherein the processing circuitry is configured to refine the classification criteria based on analysis conditions designated by an operator, and display the relevant factors for each of the refined classification criteria.

4. The medical information processing apparatus according to claim 3, wherein the processing circuitry is configured to:
display, on the display, first information for each of types and implementation timings of the medical action and second information for each of types and occurrence timings of the difference, the first information associating a type and implementation timing of the medical action, the second information associating a type and occurrence timing of the difference;
receive, from an operator, an operation selecting at least one combination of the first and second information as the analysis conditions from the displayed first and second information; and
refine the classification criteria by selecting classification criteria corresponding to the at least one combination.

5. The medical information processing apparatus according to claim 4, wherein the processing circuitry is configured to display the first information in a display mode indicating implementation frequency of the medical action and display the second information in a display mode indicating occurrence frequency of the difference.

6. The medical information processing apparatus according to claim 1, wherein the processing circuitry is configured to determine a display order of the relevant factors in accordance with a correlation value representing a degree of correlation between the relevant factors and the difference or distribution of the correlation value.

7. The medical information processing apparatus according to claim 6, wherein the processing circuitry is configured to determine the display order of the relevant factors so that a relevant factor of which the correlation value is larger is displayed on an upper side for each of the classification criteria.

8. The medical information processing apparatus according to claim 1, wherein the processing circuitry is configured to:
aggregate the relevant factors for each first classification criterion, and thereafter further aggregate the aggregated relevant factors for each second classification criterion defined as a subclassification of the first classification criteria; and
display the aggregated relevant factors for each second classification criterion in regard to the first classification criteria.

9. A medical information processing method, comprising:
obtaining first data on medical actions and second data on differences between planned medical actions or achievement objectives of treatment and results thereof;
extracting, based on the first data and the second data, relevant factors that are medical actions or achievement objectives associated with the differences and produce association rule data;
classifying the relevant factors into a plurality of classification criteria each including a plurality of elements to characterize the medical actions or achievement objectives, and correlate the elements to the classified relevant factors for each of the classification criteria and produce association rule classification data;
aggregating the classified relevant factors for each of the correlated elements of each of the classification criteria, thereby classifying the association rule classification data; and
displaying aggregated the relevant factors with the correlated elements on a display for each of the correlated elements of each of the classification criteria.

10. The medical information processing method according to claim 9, comprising defining classification criteria based on at least one of a purpose of analysis, a time, a medical care cost, complexity of the relevant factors, order type, and a relation with an item of a medical care plan or medical care flow.

11. The medical information processing method according to claim 9, comprising refining the classification criteria based on analysis conditions designated by an operator, and display the relevant factors for each of the refined classification criteria.

12. The medical information processing method according to claim 11, comprising:
  displaying, on the display, first information for each of types and implementation timings of the medical action and second information for each of types and occurrence timings of the difference, the first information associating a type and implementation timing of the medical action, the second information associating a type and occurrence timing of the difference;
  receiving, from an operator, an operation selecting at least one combination of the first and second information as the analysis conditions from the displayed first and second information; and
  refining the classification criteria by selecting classification criteria corresponding to the at least one combination.

13. The medical information processing method according to claim 12, comprising displaying the first information in a display mode indicating implementation frequency of the medical action and display the second information in a display mode indicating occurrence frequency of the difference.

14. The medical information processing method according to claim 9, comprising determining a display order of the relevant factors in accordance with a correlation value representing a degree of correlation between the relevant factors and the difference or distribution of the correlation value.

15. The medical information processing method according to claim 14, determining the display order of the relevant factors so that a relevant factor of which the correlation value is larger is displayed on an upper side for each of the classification criteria.

16. The medical information processing method according to claim 9, comprising:
  aggregating the relevant factors for each first classification criterion, and thereafter further aggregate the aggregated relevant factors for each second classification criterion defined as a subclassification of the first classification criteria; and
  displaying the aggregated relevant factors for each second classification criterion in regard to the first classification criteria.

* * * * *